US008798992B2

(12) United States Patent
Gay et al.

(10) Patent No.: US 8,798,992 B2
(45) Date of Patent: Aug. 5, 2014

(54) AUDIO NOISE MODIFICATION FOR EVENT BROADCASTING

(75) Inventors: Michael Gay, Collinsville, CT (US); Jed Drake, Simsbury, CT (US); Anthony Bailey, Wallingford, CT (US)

(73) Assignee: Disney Enterprises, Inc., Burbank, CA (US)

( * ) Notice: Subject to any disclaimer, the term of this patent is extended or adjusted under 35 U.S.C. 154(b) by 498 days.

(21) Appl. No.: 13/110,103

(22) Filed: May 18, 2011

(65) Prior Publication Data

US 2011/0288858 A1 Nov. 24, 2011

Related U.S. Application Data

(60) Provisional application No. 61/346,085, filed on May 19, 2010.

(51) Int. Cl.

| | |
|---|---|
| ***G10L 21/00*** | (2013.01) |
| ***G10L 21/02*** | (2013.01) |
| ***G10L 15/00*** | (2013.01) |
| ***G10L 15/20*** | (2006.01) |
| ***G06F 17/20*** | (2006.01) |
| ***A61F 11/06*** | (2006.01) |
| ***G10K 11/16*** | (2006.01) |
| ***H03B 29/00*** | (2006.01) |
| ***H04B 3/20*** | (2006.01) |
| ***H04B 15/00*** | (2006.01) |
| ***H03G 3/00*** | (2006.01) |
| ***H04R 25/00*** | (2006.01) |
| *H04R 9/08* | (2006.01) |
| *H04R 11/04* | (2006.01) |
| *H04R 17/02* | (2006.01) |
| *H04R 19/04* | (2006.01) |
| *H04R 21/02* | (2006.01) |

(52) U.S. Cl.

USPC ........... 704/226; 704/233; 704/234; 704/262; 704/207; 704/1; 381/71.2; 381/94.1; 381/313; 381/107; 381/23.1; 381/71.11; 381/317; 381/66; 381/359

(58) Field of Classification Search

USPC ..................... 704/226, 1, 233–234, 262, 207; 381/71.2, 94.1, 313, 107, 23.1, 71.11, 381/317, 66, 359

See application file for complete search history.

(56) References Cited

U.S. PATENT DOCUMENTS

| | | | | |
|---|---|---|---|---|
| 5,524,148 A * | 6/1996 | Allen et al. | .................. | 379/391 |
| 6,047,253 A * | 4/2000 | Nishiguchi et al. | ........... | 704/207 |

(Continued)

FOREIGN PATENT DOCUMENTS

| | | |
|---|---|---|
| WO | WO 02/18969 | 3/2002 |

OTHER PUBLICATIONS

Handbook Acoustics, Wiley, J. Crocker(Editor), 1998, pp. 1341-1353.

(Continued)

*Primary Examiner* — Paras D Shah
*Assistant Examiner* — Anne Thomas-Homescu
(74) *Attorney, Agent, or Firm* — Buckley, Maschoff & Talwalkar LLC

(57) ABSTRACT

An signal processing apparatus, system and software product for audio modification/substitution of a background noise generated during an event including, but not be limited to, substituting or partially substituting a noise signal from one or more microphones by a pre-recorded noise, and/or selecting one or more noise signals from a plurality of microphones for further processing in real-time or near real-time broadcasting.

16 Claims, 6 Drawing Sheets

(56) References Cited

U.S. PATENT DOCUMENTS

| | | | | |
|---|---|---|---|---|
| 6,449,586 | B1 | 9/2002 | Hoshuyama | |
| 6,888,949 | B1 | 5/2005 | Vanden Berghe et al. | |
| 7,333,863 | B1 * | 2/2008 | Lydecker et al. | 700/94 |
| 8,046,219 | B2 * | 10/2011 | Zurek et al. | 704/233 |
| 8,280,065 | B2 * | 10/2012 | Nadjar et al. | 381/71.1 |
| 8,515,257 | B2 * | 8/2013 | Harrington | 386/285 |
| 2003/0093270 | A1 * | 5/2003 | Domer | 704/227 |
| 2004/0167767 | A1 * | 8/2004 | Xiong et al. | 704/1 |
| 2005/0141731 | A1 | 6/2005 | Hamaliainen | |
| 2005/0147258 | A1 * | 7/2005 | Myllyla et al. | 381/71.11 |
| 2005/0149320 | A1 | 7/2005 | Kajala | |
| 2005/0195998 | A1 * | 9/2005 | Yamamoto et al. | 381/119 |
| 2007/0106507 | A1 * | 5/2007 | Charoenruengkit et al. | 704/233 |
| 2007/0294087 | A1 * | 12/2007 | Lakaniemi | 704/262 |
| 2008/0004875 | A1 * | 1/2008 | Chengalvarayan et al. | 704/234 |
| 2009/0060216 | A1 * | 3/2009 | Sweeney et al. | 381/71.2 |
| 2009/0265022 | A1 * | 10/2009 | Kirovski et al. | 700/94 |
| 2011/0257967 | A1 * | 10/2011 | Every et al. | 704/226 |
| 2011/0305345 | A1 * | 12/2011 | Bouchard et al. | 381/23.1 |
| 2012/0008802 | A1 * | 1/2012 | Felber | 381/107 |
| 2012/0008807 | A1 * | 1/2012 | Gran | 381/313 |
| 2012/0020489 | A1 * | 1/2012 | Narita | 381/71.1 |
| 2012/0123772 | A1 * | 5/2012 | Thyssen et al. | 704/226 |
| 2012/0179461 | A1 * | 7/2012 | Every et al. | 704/226 |
| 2012/0207315 | A1 * | 8/2012 | Kimura et al. | 381/66 |
| 2012/0257779 | A1 * | 10/2012 | Kimura et al. | 381/359 |
| 2013/0034243 | A1 * | 2/2013 | Yermeche et al. | 381/94.1 |
| 2013/0080158 | A1 * | 3/2013 | Hetherington et al. | 704/226 |
| 2013/0108092 | A1 * | 5/2013 | Litvak et al. | 381/317 |
| 2013/0204617 | A1 * | 8/2013 | Kuo et al. | 704/233 |
| 2013/0211830 | A1 * | 8/2013 | Petit et al. | 704/226 |

OTHER PUBLICATIONS

Handbook for Sound Engineers: The New Audio Cyclopedia, Sams, Glen Ballou(Editor), Second Edition, 1991, pp. 393-495.

* cited by examiner

AUDIO NOISE MODIFICATION FOR EVENT BROADCASTING

CROSS-REFERENCE TO RELATED APPLICATION

This non-provisional U.S patent application claims priority to U.S. Provisional Patent Application No. 61/346,085 filed May 19, 2010 which is incorporated herein by reference.

BACKGROUND OF INVENTION

The present invention relates generally to audio processing, and more specifically, to audio modification/substitution of a background noise generated during an event, e.g., during a sport event at a stadium.

Audio processing of a background noise during an event (e.g., a background noise during a sport event or during any performance in front of an audience) may represent a challenge. On one hand it is desirable to have a background noise during broadcasting of the event, e.g., along the voice of a commentator, to convey the reaction of an audience (e.g., applause, cheering), sounds related to the event itself (e.g., ball hit) and/or event procedural announcements or music, etc. This type of a background noise is desirable and is a "good" noise.

On the other hand, the challenge for the background noise processing is that some background noise sounds may be extremely loud causing an interference with the production audio (e.g., a commentator voice), which may be distracting to viewers of the event watching the event via television, computers or any other means. Such a loud noise is a "bad" noise which is highly undesirable and should be cancelled/reduced for eliminating its interfering with broadcasting.

The previous solutions utilizing standard noise cancellation using hardware and/or software solutions typically do not have an intelligence to distinguish between "good" and "bad" noises, e.g., a standard noise cancellation does not have an intelligence of discerning between different acoustic (audio) frequencies of the background noise. Also the standard noise cancellation solutions are relatively slow in order to achieve a desirable real-time performance.

BRIEF SUMMARY OF INVENTION

According to a first aspect of the present invention, an apparatus comprises: a detector-analyzer, configured to receive noise signals from a plurality of microphones and to provide indicator signals for the noise signals; and a controller, configured to provide comparing of information comprised in the each indicator signal with one or more preset threshold values and identifying, if available, one or more indicator signals out of the indicator signals meeting one or more predetermined criteria using the comparing, and to provide a first control signal for selecting out of the noise signals one or more noise signals corresponding to the one or more indicator signals for combining the one or more noise signals if the one or more noise signals comprise only one noise signal, or the one or more noise signals after being further modified, with one or more voice signals provided by one or more further microphones.

In further accord with the first aspect of the invention, the one or more preset threshold values, for at least one parameter comprised in each indicator signal of the indicator signals, may comprise two values THR-1 and THR-2, wherein THR-2 is larger than THR-1, and if the at least one parameter is larger than THR-2 then a noise signal corresponding to the each indicator signal may not be selected, if the one parameter is larger than THR-1 but smaller than THR-2 then the noise signal corresponding to the each indicator may be selected and further modified, and if the one parameter is smaller than THR-1 then the noise signal corresponding to the each indicator may be selected without further modification.

Still according to the first aspect of the invention, each indicator signal of the indicator signals may comprise one or more of: an average power, a root-mean-square power, a peak power and one or more characteristics of an acoustic spectrum for corresponding each of the noise signals.

According still further to the first aspect of the invention, said apparatus may further comprise: a signal selector, configured to select the one or more noise signals out of the noise signals in response to the first control signal.

Still further according to the first aspect of the invention, the controller may be configured to provide a further control signal, and the apparatus may further comprise: a noise modification module, configured to modify in response to the further control signal the one or more noise signals before the combining with one or more voice signals using one or more of: statistically averaging the one or more noise signals using a pre-defined algorithm, if the one or more signals comprise at least two noise signals, adjusting an average power, peak power or one or more amplitude spectral peaks in one or selected noise signals of the one or more noise signals, removing one or more undesired frequency components in corresponding one or more frequency bands in one or selected noise signals of the one or more noise signals, and filling the one or more frequency bands with matching pre-recorded noise signals or with matching pre-recorded noise signals after being further modified in response to the further control signal.

In further accordance with the first aspect of the invention, the apparatus may further comprise: a database, configured to store pre-recorded noises, wherein the controller may be configured to provide a second control signal to the database in order to provide a matching pre-recorded noise signal selected from the pre-recorded noises stored in the database.

Yet further still according to the first aspect of the invention, wherein the controller does not find one or more indicator signals out of the indicator signals meeting one or more predetermined criteria using the comparing, such that the controller may be configured to provide a second control signal to provide a matching pre-recorded noise signal for combining the matching pre-recorded noise signal with the one or more voice signals provided by the one or more further microphone.

According further to the first aspect of the invention, the apparatus may further comprise: a combiner, configured to combine in a real-time or in a near real-time the one or more noise signals if the one or more noise signals comprises only one noise signal, the one or more noise signals after being further modified, or a matching pre-recorded noise signal with the one or more voice signals provided by the one or more further microphones is performed in a real-time or in a near real-time.

According still further to the first aspect of the invention, the plurality of microphones may be placed in a stadium in different locations.

According yet further to the first aspect of the invention, the one or more further microphones may be one or more voice microphones configured to reject a low background noise and the plurality of microphones are omni-directional microphones.

Further still according to the first aspect of the invention, an integrated circuit may comprise all or selected modules of the apparatus.

According to a second aspect of the invention, a method, comprises: providing by a detector-analyzer indicator signals for each of noise signals received from a plurality of microphones; and comparing, by a controller, information comprised in each indicator signal of the indicator signals with one or more preset threshold values and identifying, if available, one or more indicator signals out of the indicator signals meeting one or more predetermined criteria using the comparing; providing by the controller a first control signal for selecting out of the noise signals one or more noise signals corresponding to the one or more indicator signals; and combining the one or more noise signals if the one or more noise signals comprise only one noise signal, or the one or more noise signals after being further modified, with one or more voice signals provided by one or more further microphones.

According further to the second aspect of the invention, each indicator signal of the indicator signals may comprise one or more of: an average power, a root-mean-square power, a peak power and one or more characteristics of an acoustic spectrum for corresponding each of the noise signals.

Further according to the second aspect of the invention, the one or more preset threshold values, for at least one parameter comprised in each indicator signal of the indicator signals, may comprise two values THR-1 and THR-2, wherein THR-2 is larger than THR-1, and if the at least one parameter is larger than THR-2 then a noise signal corresponding to the each indicator signal may not be selected, if the one parameter is larger than THR-1 but smaller than THR-2 then the noise signal corresponding to the each indicator may be selected and further modified, and if the one parameter is smaller than THR-1 then the noise signal corresponding to the each indicator may be selected without further modification.

Still further according to the second aspect of the invention, wherein before the combining, the method may further comprise: selecting the one or more noise signals out of the noise signals in response to a first control signal; and modifying in response to a further control signal provided by the controller the one or more noise signals before the combining with the one or more voice signals using one or more of: statistically averaging the one or more noise signals using a pre-defined algorithm, if the one or more signals comprise at least two noise signals, if the one or more signals comprise at least two noise signals, adjusting an average power, peak power or one or more amplitude spectral peaks in one or selected noise signals of the one or more noise signals, removing one or more undesired frequency components in corresponding one or more frequency bands in one or selected noise signals of the one or more noise signals, and filling the one or more frequency bands with matching pre-recorded noise signals or with matching pre-recorded noise signals after being further modified in response to the further control signal.

Further still in accordance with the second aspect of the invention, the controller does not find any indicator signal out of the indicator signals meeting one or more predetermined criteria using the comparing, such that the method may further comprise: providing, in response to a second control signal provided by the controller, a matching pre-recorded noise signal selected from the pre-recorded noises stored in the database for combining the matching pre-recorded noise signal with the one or more voice signals provided by the one or more further microphone.

Still further according to the second aspect of the invention, the combining of the one or more noise signals, if the one or more noise signals comprises only one noise signal, the one or more noise signals after being further modified, or a matching pre-recorded noise signal with the one or more voice signals provided by the one or more further microphones, may be performed in a real-time or in a near real-time.

Yet further still according to the second aspect of the invention, the plurality of microphones may be placed in a stadium in different locations.

According to a third aspect of the present invention, a computer readable medium encoded with a computer program comprising computer readable instructions recorded thereon for execution a method which comprises: providing by a detector-analyzer indicator signals for each of noise signals received from a plurality of microphones; comparing, by a controller, information comprised in each indicator signal of the indicator signals with one or more preset threshold values and identifying, if available, one or more indicator signals out of the indicator signals meeting one or more predetermined criteria using the comparing; providing by the controller a first control for selecting out of the noise signals one or more noise signals corresponding to the one or more indicator signals; and combining the one or more noise signals if the one or more noise signals comprise only one noise signal, or the one or more noise signals after being further modified, with one or more voice signals provided by one or more further microphones.

According to a fourth aspect of the present invention, a system, comprises: a plurality of microphones configured to provide noise signals during an event; one or further microphones configured to provide voice signals and reject background noise signals; and an apparatus comprising a detector-analyzer, configured to receive noise signals from the plurality of microphones and to provide indicator signals for the noise signals; and a controller, configured to provide comparing of information comprised in the each indicator signal with one or more preset threshold values and identifying, if available, one or more indicator signals out of the indicator signals meeting one or more predetermined criteria using the comparing, and to provide a first control signal for selecting out of the noise signals one or more noise signals corresponding to the one or more indicator signals for combining the one or more noise signals if the one or more noise signals comprise only one noise signal, or the one or more noise signals after being further modified, with one or more voice signals provided by the one or more further microphones.

According to a fifth aspect of the invention, an apparatus, comprises: a detector-analyzer, configured to receive a noise signal from a microphone and to provide an indicator signal for the noise signal; and a controller, configured to provide comparing of information comprised in the indicator signal with one or more preset threshold values and determining if a substitution of the noise signal by a matching pre-recorded noise signal is necessary based on a predetermined criterion using the comparing, and to provide a first control signal for selecting or de-selecting the noise signal and, if the substitution is necessary, to provide a second control signal for substituting the noise signal by the matching pre-recorded noise signal, for combining the matching pre-recorded noise signal, the noise signal or the noise signal after being further modified, with one or more voice signals provided by one or more further microphones.

According further to the fifth aspect of the invention, the indicator signal may comprise one or more of: an average power, a root-mean-square power, a peak power and one or more characteristics of an acoustic spectrum for the noise signal.

Further according to the fifth aspect of the invention, the apparatus may further comprise: a signal selector, configured to select or de-select the noise signal in response to the first control signal.

Still further according to the fifth aspect of the invention, the apparatus may further comprise: a combiner, configured to combine the noise signal, the noise signal after being further modified or the matching pre-recorded noise signal with one or more voice signals provided by one or more further microphones.

Further still in accordance with the fifth aspect of the invention, the one or more of the further microphones may be one or more voice microphones configured to reject background noise, and the microphone may be an omni-directional microphone.

In further accordance with the fifth aspect of the invention, the controller may be configured to provide a further control signal, and the apparatus may further comprise: a noise modification module, configured to modify in response to the further control signal the noise signal before the combining with the one or more voice signals using one or more of: adjusting an average power, peak power or one or more amplitude spectral peaks, removing one or more undesired frequency components in corresponding one or more frequency bands, and filling the one or more frequency bands with matching pre-recorded noise signals or with matching pre-recorded noise signals after being further modified in response to the further control signal.

Yet further still according to the fifth aspect of the invention, the one or more preset threshold values for at least one parameter comprised in the indicator signal, may comprise two values THR-1 and THR-2, wherein THR-2 is larger than THR-1, and if the at least one parameter is larger than THR-2 then a noise signal corresponding to the indicator signal may be de-selected, if the one parameter is larger than THR-1 but smaller than THR-2 then the noise signal may be selected and further modified, and if the one parameter is smaller than THR-1 then the noise signal may be selected without further modification.

According still further to the fifth aspect of the invention, the combining of the matching pre-recorded noise signal, the noise signal or the noise signal after being further modified, with one or more voice signals provided by the one or more further microphones may be performed in a real-time or in a near real-time.

According yet further to the fifth aspect of the invention, the apparatus may further comprise: a database, configured to store pre-recorded noises, wherein the controller is configured to provide the second control signal to the database for providing the matching pre-recorded noise signal selected from the pre-recorded noises stored in the database.

Further still according to the fifth aspect of the invention, the microphone and one or more voice microphones may be located in a stadium.

Yet still further according to the fifth aspect of the invention, an integrated circuit may comprise all or selected modules of the apparatus.

According to a sixth aspect of the present invention, a method, comprises: providing by a detector-analyzer an indicator signal for a noise signal received from a microphone; comparing by a controller information comprised in the indicator signal with one or more preset threshold values and determining if a substitution of the noise signal by a matching pre-recorded noise signal is necessary based on a predetermined criterion using the comparing; selecting or de-selecting the noise signal based on the determining, and, if the substitution is necessary, substituting the noise signal by the matching pre-recorded noise signal; and combining the matching pre-recorded noise signal, the noise signal or the noise signal after being further modified, with one or more voice signals provided by one or more further microphones.

In further accord with the sixth aspect of the invention the indicator signal may comprise one or more of: an average power, a root-mean-square power, a peak power and one or more characteristics of an acoustic spectrum for the noise signal.

Still yet further according to the sixth aspect of the invention, the selecting or de-selecting of the noise signal may be performed in response to a first control signal provided by a controller based on the determining.

Still according to the sixth aspect of the invention, the one or more preset threshold values for at least one parameter comprised in the indicator signal, may comprise two values THR-1 and THR-2, wherein THR-2 is larger than THR-1, and if the at least one parameter is larger than THR-2 then a noise signal corresponding to the indicator signal may be de-selected, if the one parameter is larger than THR-1 but smaller than THR-2 then the noise signal may be selected and further modified, and if the one parameter is smaller than THR-1 then the noise signal may be selected without further modification.

Still further according to the sixth aspect of the invention, the one or more further microphones may be voice microphones configured to reject background noise, and the microphone may be an omni-directional microphone.

Further still according to the sixth aspect of the invention, before the combining with the one or more voice signals, the method may further comprise: providing a further control signal by the controller; modifying in response to the further control signal the noise signal using one or more of: adjusting an average power, peak power or one or more amplitude spectral peaks, removing one or more undesired frequency components in one or more frequency bands, and filling the one or more frequency bands with the matching pre-recorded noise signal or with the matching pre-recorded noise signal after being further modified in response to the further control signal.

In further accordance with the sixth aspect of the invention, the combining of the matching pre-recorded noise signal, the noise signal or the noise signal after being further modified, with one or more voice signals provided by the one or more further microphones may be performed in a real-time or in a near real-time.

Yet further still according to the sixth aspect of the invention, the microphone and the one or more voice microphones may be located in a stadium.

According to a seventh aspect of the present invention, a computer readable medium encoded with a computer program comprising computer readable instructions recorded thereon for execution a method which comprises: providing by a detector-analyzer an indicator signal for a noise signal received from a microphone; comparing by a controller information comprised in the indicator signal with one or more preset threshold values and determining if a substitution of the noise signal by a matching pre-recorded noise signal is necessary based on a predetermined criterion using the comparing; selecting or de-selecting the noise signal based on the determining, and, if the substitution is necessary, substituting the noise signal by the matching pre-recorded noise signal; and combining the matching pre-recorded noise signal, the noise signal or the noise signal after being further modified, with one or more voice signals provided by one or more further microphones.

According to an eighth aspect of the present invention, a system, comprises: a microphone configured to provide a noise signal during an event; one or more further microphones configured to provide one or more voice signals and reject background noise signals; and an apparatus, comprising a detector-analyzer, configured to receive a noise signal from a microphone and to provide an indicator signal for the noise signal; and a controller, configured to provide comparing of information comprised in the indicator signal with one or more preset threshold values and determining if a substitution of the noise signal by a matching pre-recorded noise signal is necessary based on a predetermined criterion using the comparing, and to provide a first control signal for selecting or de-selecting the noise signal and, if the substitution is necessary, to provide a second control signal for substituting the noise signal by the matching pre-recorded noise signal, for combining the matching pre-recorded noise signal, the noise signal or the noise signal after being further modified, with one or more voice signals provided by one or more further microphones.

DESCRIPTION OF THE DRAWINGS

For a better understanding of the nature and objects of the present invention, reference is made to the following detailed description taken in conjunction with the following drawings, in which.

DETAILED DESCRIPTION OF EMBODIMENTS

Figure 1:
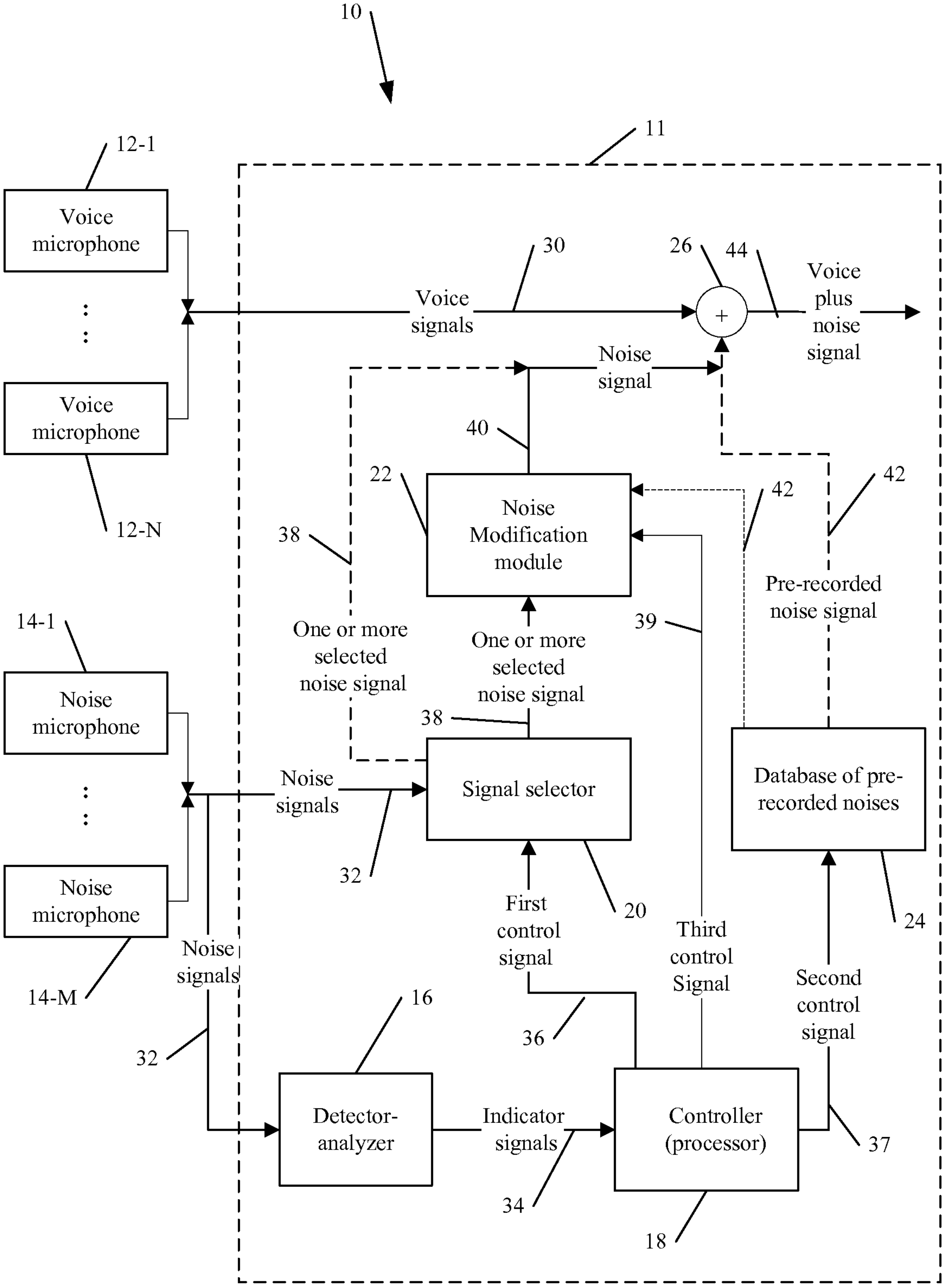
FIG. 1 is a time diagram demonstrating a time dependence of a parameter of a background noise signal provided by a noise dedicated microphone for evaluating this parameter using a two preset threshold values, according to an embodiment of the present invention.

In embodiments a new method, apparatus, system and software product (e.g., a computer readable medium) are presented for audio modification/substitution of a background noise generated during an event including, but not be limited to, substituting or partially substituting (e.g., in a identified audio spectral band) a noise signal from one or more microphones by a pre-recorded noise, and/or selecting one or more noise signals from a plurality of microphones for further processing in real-time broadcasting or near real-time broadcasting with a purpose of providing the background noise corresponding to a content of the event but not exceeding an acceptable signal threshold(s) and therefore not distracting the viewers/listeners of the event during broadcasting of the event (e.g., using television, computer, radio, etc.). The event may be a sport event at a stadium, a soccer match, a sporting event in general, a concert, a performance in front of an audience, etc. The implementation of different embodiments disclosed herein may be performed in analog and/or digital domains, as well as using hardware and/or software solutions.

It is noted that for a purpose of this invention a term "near real-time broadcasting" means that a time difference between an image and a tracking sound of the broadcasting, or, e.g., between a voice of a commentator and a noise content during the event is practically unnoticeable by a viewer or by a listener.

According to one embodiment, one or more dedicated voice microphones may be used for detecting a voice (e.g., speech) only and rejecting any other background noises, i.e., forming a "voice channel" in the real-time or in the near real-time. Then, one or more dedicated noise microphones/microphone processing system(s), separate from the one or more dedicated voice microphones, may be used for detecting/modification/substitution of a background noise, i.e., forming a "noise channel" in the real-time or in the near real-time. These one or more noise microphones may be placed at different locations relative to the voice microphone(s) and at different locations relative to each other, e.g., in a stadium.

Using one microphone or multiple microphones with corresponding processing system(s) just for the voice (e.g., speech) recording and rejecting any other background noises is known in the art. One possibility may be recording in a studio acoustically isolated from the background noise. Another option may be using a highly directional microphone, e.g., a unidirectional or a noise-cancelling microphone or the likes to detect (or predominantly detect) only a human voice in a close proximity to the microphone and reject other background noises (e.g., see review of the microphones in "Handbook for Sound Engineers: The New Audio Cyclopedia", SAMS, Glen Ballou (Editor), Second Edition, 1991 pp. 393-4-95). Also, more sophisticated processing methods may be used, including (but not limited to) the use of multiple microphones or an array of microphones and using a beamformer technique and/or an adaptation control for noise cancellation, e.g., see U.S. Pat. No. 6,449,586 (Control Method of Adaptive Array and Adaptive Control Apparatus by O. Hoshuyama); U.S. Pat. No. 6,888,949 (Hearing Aid with Adaptive Noise Canceller by J. V. Berghe), International Publication Number WO-02/18969 (System and Method for Processing a Signal Being Emitted from a Target Signal Source into a Noisy Environment by M. Kajala), US Patent Application Publication No. US2005-0147258 (Method for Adjusting Adaptation Control of Adaptive Interference Canceller by V. Myllyla et al.), US Patent Application Publication No. US2005-0149320 (Method for Generating Noise References for Generalized Sidelobe Canceling by M. Kajala), US Patent Application Publication No. US2005-0141731 (Method for Efficient Beamforming using a Complimentary Noise Separation Filter by M. Hamaliainen), etc.

According to an embodiment A when using one dedicated voice microphone or a plurality of dedicated voice microphones (e.g., in case of several reporters providing simultaneous broadcasting of a sporting event using separate dedicated voice microphones) and using a plurality of dedicated noise microphones, a detector-analyzer of a processing device (i.e., an apparatus) may receive noise signals from a plurality of these noise dedicated microphones and may provide indicator signals for the corresponding noise signals, wherein each indicator signal may provide one or more measured parameters of the noise signals (e.g., measured by a detector-analyzer) such as an average power, a root-mean-square power, a peak power, one or more characteristics/parameters of an acoustic spectrum such as a number, an amplitude and/or a spectral width of peaks, etc. for corresponding each of the noise signals (e.g., see review of the audio signal analyzers in "Handbook Acoustics, Wiley, Malcolm J. Crocker (Editor), 1998 pp. 1341-1353). The detector-analyzer may be a dedicated analog module or digital module, a device or a general-purpose computer equipped with appropriate means and suitable application software. For example, an average power, a root-mean-square (RMS) power or a peak power of the noise signal may be measured by a level detector, an RMS detector or a peak detector, respectively. The acoustic spectrum (in a frequency domain) may be measured, e.g., using a basic sound level meter (such as a root-mean-square detector) in combination with a filter set. More advanced frequency analyzers may use digital techniques such as Discrete Fourier Transform (e.g., an FFT—Fast Fourier Transform) analysis, as known in the art.

Moreover, according to the embodiment A disclosed herein, a controller (e.g., a processor) may compare information comprised in each indicator signal with one or more preset threshold values (e.g., threshold value for an average power, an RMS power, a peak amplitude, an amplitude and a bandwidth of a spectral peak in the acoustic spectrum, etc.) and then to identify, if available, one or more indicator signals (out of the indicator signals for the corresponding noise signals) meeting one or more predetermined criteria. Then such a controller may coordinate further processing, first, by providing a first control signal to select one or more noise signals (out of all noise signals provided by the plurality of the dedicated noise microphones) corresponding to the identified indicator signals, which may be implemented, e.g., by a signal selector. Then the controller may provide a further control signal for a modification of the selected one or more noise signals before combining them with the one or more voice signals provided by the one or more dedicated voice microphones. Alternatively, this modification may be performed by default (e.g., for performing statistical averaging for the one or more noise signals as further disclosed herein). The modification of the selected one or more noise signals may include but may not be limited to the following options:

a) statistically averaging in time domain the selected one or more noise signals, if these one or more noise signals comprise at least two noise signals, for example, by combining these one or more noise signals using a pre-defined algorithm such as summing with equal weights for the selected noise signals, summing with unequal weights for the noise signals depending on the "quality" of the noise signals (and their ranking) which may be determined by the controller and provided in this further control signal: for instance, this "quality" may be defined by a number of peaks and/or peaks amplitudes in the acoustic spectrum of the noise signals; and/or b) optionally adjusting an average power, a peak power, and/or spectral peak(s) in the acoustic spectrum in one or selected noise signals of the selected one or more noise signals; for example, if it is determined by the controller that some of the selected noise signals may have an average (or peak) power exceeding a first preset threshold value but being below a second preset threshold value, the controller may include in the further control signal a request to attenuate such a noise signal by a certain amount, e.g., to bring the average (or peak) power below the first preset threshold value (as further explained herein) before performing the averaging disclosed in a); also if it is determined by the controller that a spectral peak in the acoustic spectrum in a particular noise signal may have the amplitude exceeding the first preset threshold value but being below the second preset threshold value, the controller may include in the further control signal a request to attenuate this spectral peak of such noise spectral component in the noise signal by a certain amount using spectral filtering, e.g., to bring the amplitude of the spectral peak below the first preset threshold value before performing the averaging disclosed in a); in addition, the further control signal may comprise a request to attenuate the noise after the averaging disclosed in a) if it is found that all selected noise signals have the average power and/or the peak power exceeding the first preset threshold value but being below the second preset threshold value; and/or c) optionally removing one or more undesired frequency components in one or more frequency bands in one or selected noise signals of the one or more selected noise signals; for example, if all selected one or more noise signals have a number of spectral peaks and/or peak amplitudes in the acoustic spectrum of the noise signals exceeding the first preset threshold value but being below the second preset threshold value, as disclosed herein, then the controller may include in the further control signal a request to remove these one or more undesired frequency components in the one or more frequency bands in these one or selected noise signals; and/or d) optionally filling the one or more frequency bands comprising removed frequency components as disclosed in c) with matching one or more pre-recorded noise signals; for example, the controller may be configured to provide another control signal to a database which may store a library of pre-recorded noises in order to provide a matching pre-recorded noise signal using these pre-recorded noises stored in the database. There are a few of known techniques which may be used for generating such pre-recorded noises, e.g., background noises of different types during a sporting event; examples of extracting sport highlights from audio signals classified as applause, cheering, ball hit, music, voice and music, etc. is disclosed in US Patent Application Publication No. 2004/0167767 (Method and system for Extracting Sports Highlights from Audio Signals by Z. Xiong et al.); the pre-recorded noises may be classified by their content, average power, spectral content, etc., such that the controller may be able to select a pre-recorded noise closely matching desired characteristics/parameters of the noise for substituting the noise signal having at least one measured parameter exceeding the second preset threshold level as measured by the detector-analyzer (e.g., the spectral content, the average or peak power, etc.); it is also noted that the pre-recorded noises may be further modified, if necessary, to match a particular noise requirements per an additional instruction from the controller.

Furthermore, according to the embodiment A, if the controller may find that none of the indicator signals for the noise signals meet one or more predetermined criteria, then the controller may provide a still further control signal to the database storing a library of the pre-recorded noises in order to provide a matching pre-recorded noise signal for combining the matching pre-recorded noise signal with the one or more voice signals provided by the one or more voice microphones.

Finally, according to the embodiment A, a combiner may combine the selected one or more noise signals (e.g., if only one noise signal is selected), said one or more noise signals after being further modified, or a matching pre-recorded noise signal (original or after being further modified) with the one or more voice signals provided by the one or more voice microphones possibly in the real-time or near real-time.

According to an embodiment B when using one dedicated voice microphone or a plurality of dedicated voice microphones (e.g., in case of several reporters providing broadcasting of a sporting event) and using only one dedicated noise microphone, the detector-analyzer of a processing device (i.e., an apparatus) may receive a noise signal from the noise dedicated microphone and provide an indicator signal for this noise signal, wherein the indicator signal may provide one or more measured parameters of the noise signal, e.g., measured by a detector-analyzer, such as an average power, a root-mean-square power, a peak power, one or more characteristics/parameters of an acoustic spectrum such as a number, an amplitude and/or a spectral width of peaks, etc. for the noise signals (e.g., see review of the audio signal analyzers in "Handbook Acoustics, Wiley, Malcolm J. Crocker (Editor), 1998 pp. 1341-1353). The detector-analyzer may be a dedicated analog module or a digital module, a device or a general-purpose computer equipped with appropriate means and suitable application software. For example, an average power, a root-mean-square (RMS) power or a peak power of the noise signal may be measured by a level detector, an RMS detector or a peak detector, respectively. The acoustic spectrum (in the frequency domain) may be measured, e.g., using a basic sound level meter (such as a root-mean-square detector) in combination with a filter set. More advanced frequency analyzers may use digital techniques such as Discrete Fourier Transform (e.g., an FFT—Fast Fourier Transform) analysis, as known in the art. It is noted that the difference between the embodiments A and B is that in the embodiment B there is only one dedicated noise microphone, whereas in the embodiment A there are a plurality of the dedicated noise microphones, but the algorithm for providing the indicator signal in the embodiment B and multiple indicators (corresponding to the multiple noise signals) in the embodiment A is similar. However in the embodiment A, a multi-channel detector-analyzer may be used for processing a plurality of the noise signals, or multiple detector-analyzers may be used for that processing, each detector-analyzers being dedicated to one noise signal of this plurality of the noise signals.

Moreover, according to the embodiment B disclosed herein, a controller (e.g., a processor) may compare information comprised in the indicator signal with one or more preset threshold values (e.g., the threshold value for a measured average power, an RMS power, a peak amplitude, an amplitude and a bandwidth of a spectral peak in the acoustic spectrum, etc.) and then may determine if a substitution of the noise signal by a matching pre-recorded noise signal is necessary based on a predetermined criterion using this comparing, and to provide a first control signal for de-selecting or selecting the noise signal; then, if the noise signal is de-selected, the controller may provide a second control signal for substituting of the noise signal by a matching pre-recorded noise signal. Moreover, if the noise signal is selected, the controller may provide a further control signal for modification of the noise signal, if necessary, before combining with the one or more voice signals. Alternatively, this modification may be performed by default. The modification of the noise signal may include but may not be limited to:

a) adjusting an average power, a peak power, and/or spectral peak(s) in the acoustic spectrum in the selected noise signal; for example, if it is determined by the controller that the noise signal may have an average (or peak) power exceeding a first preset threshold value but being below a second preset threshold value, the controller may include in the further control signal a request to attenuate this noise signal by a certain amount, e.g., to bring the average (or peak) power below the first preset threshold value; also if it is determined by the controller that a spectral peak in the acoustic spectrum of the noise signal may have the amplitude exceeding the first preset threshold value but being below the second preset threshold value, the controller may include in the further control signal a request to attenuate this spectral peak of such noise spectral component in the noise signal using spectral filtering by a certain amount, e.g., to bring the amplitude of the spectral peak below the first threshold value; and/or b) removing one or more undesired frequency components in one or more frequency bands in the noise signal; for example, if the noise signal has one or more spectral peaks (or peak amplitudes) in the acoustic spectrum of the noise signal exceeding the first preset threshold value but being below the second preset threshold value, then the controller may include in the further control signal a request to remove these one or more undesired frequency components in the one or more frequency bands; and/or c) filling the one or more frequency bands with removed frequency components as disclosed in b) with matching one or more pre-recorded noise signals; for example, the controller may provide another control signal to a database which may store a library of pre-recorded noises in order to provide a matching pre-recorded noise signal using these pre-recorded noises stored in the database; these are a variety of known techniques which may be used to generate such pre-recorded noises, e.g., background noises of different types during a sporting event; examples of extracting sport highlights from audio signals classified as applause, cheering, ball hit, music, voice and music, etc. is disclosed in US Patent Application Publication No. 2004/0167767 (Method and system for Extracting Sports Highlights from Audio Signals by Z. Xiong et al.); the pre-recorded noises may be classified by their content (e.g., applause, cheering, etc.), average power, spectral content, etc., such that the controller may be able to select the pre-recorded noise closely matching measured characteristics/parameters of the noise by the detector-analyzer (e.g., the spectral content, the average or peak power, etc.); it is also noted that the pre-recorded noises may be further modified, if necessary, to match a particular noise requirements (e.g., for the average power, spectral width, etc.) in response to an additional instructions from the controller.

Furthermore, according to the embodiment B, if the controller may find that the indicator signal for the noise signal does not meet one or more predetermined criteria (e.g., at least one measured parameter comprised in the indication signal exceeding a second threshold), then the controller may provide a still further control signal to the database storing the library of the pre-recorded noises in order to provide a matching pre-recorded noise signal for combining this matching pre-recorded noise signal with the one or more voice signals provided by the one or more voice microphones.

Finally, according to the embodiment B, a combiner may combine the noise signal, the noise signals after being further modified, or a matching pre-recorded noise signal (original or after being further modified) with the one or more voice signals provided by the one or more voice microphones possibly in the real-time or near real-time.

From the discussions of the embodiments A and B, it follows that it may be more than one preset thresholds established for one parameter of the noise signal. For example, the THR-1 may be a first threshold value for a parameter (e.g., an average power) of the noise signal, such that if the measured parameter is below THR-1, then the noise signal may be selected (without modification or substitution), however if the parameter exceeds THR-1 for a particular noise signal, this noise signal may not be disqualified from a further consideration, but further evaluated against a second threshold value THR-2, wherein typically THR-2>THR-1, such that if the measured parameter of this particular noise signal exceeds THR-2, then this noise signal is not selected, however, if the measured parameter is between THR-1 and THR-2, for this noise signal, the controller may provide a request using the further control signal to modify this particular noise signal as discussed herein (e.g., to attenuate its average power across the spectrum by a certain amount to bring it below THR-1). This is illustrated in FIG. 1.

FIG. 1 shows an example among others of a time diagram demonstrating a time dependence of a parameter of a background noise signal provided by a noise dedicated microphone, and an evaluating procedure for this parameter using two preset threshold values THR-1 and THR-2, according to an embodiment of the present invention. Point 1 at the time t1 in FIG. 1 may correspond to the case wherein the measured parameter at the time t1 is above the preset threshold value THR-2, then the noise signal may not be selected at the time t1 but may be substituted by a matched pre-recorded noise signal as discussed herein in reference to the embodiments A and B. Moreover, point 2 at the time t2 in FIG. 1 may correspond to the case wherein the measured parameter at the time t2 is below the preset threshold value THR-2 but above the preset threshold value THR-1, then the noise signal may be selected at the time t2 but may be further modified as disclosed herein in the option b) discussed in reference to the embodiment A or in the option a) discussed in reference to the embodiment B. Furthermore, point 3 at the time t3 in FIG. 1 may correspond to the case wherein the measured parameter at the time t2 is below the preset threshold value THR-1, then the noise signal may be selected, such that its modification or substitution is not necessary.

It is noted that an example shown in FIG. 1 may have many variations. For example, an evaluation procedure for a particular parameter of the noise signal may have only one preset threshold value with eliminated noise modification step. For example, the threshold value THR-1 in FIG. 1 may be st to be equal to the threshold value THR-2, such that if the measured parameter at t1 being above this one preset threshold value THR-1=THR-2, the noise signal may not be selected at the time t1 but may be substituted by a matched pre-recorded noise signal as discussed herein in reference to the embodiments A and B. However, if the measured parameter at t3 being above this one preset threshold value THR-1=THR-2, the noise signal may not be selected at the time t3 such that substitution is not necessary.

It is further noted that the principle of having one preset threshold value THR-1=THR-2, as discussed herein, may be especially attractive for the embodiment B, wherein a simple measuring real-time feedback system may be used for a dynamic substitution of the background noise during a broadcasting event.

FIGS. 2-5 further illustrate various embodiments of the invention described herein.

Figure 2:
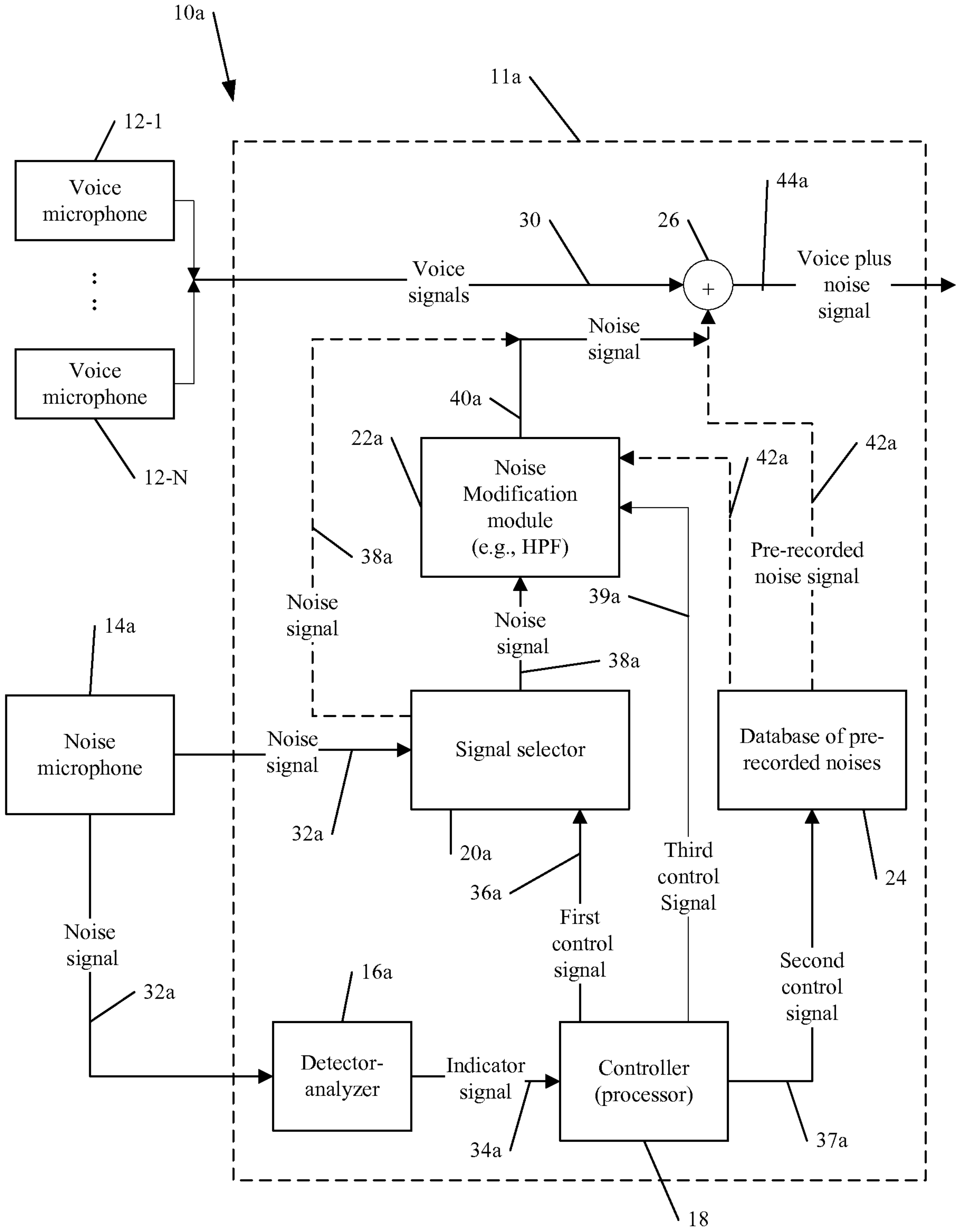
FIG. 2 is a block diagram of a multiple-microphone system for noise modification, the system comprising one or more voice microphones and a plurality of microphones for detecting a background noise during an event, according to an embodiment of the present invention.

FIG. 2 shows an example among others of a block diagram of a multiple-microphone system 10 for audio modification of a background noise illustrating the embodiment A as disclosed herein. The system 10 may comprise one or more dedicated voice microphones 12-1, 12-2, . . . , 12-N, N being an integer of a value of one or more, and a plurality of dedicated noise microphones (which may be called "noise microphones") 14-1, 14-2, . . . , 14-M, M being an integer of a value of two or more, dedicated to detecting a background noise during the event, according to an embodiment of the present invention. An apparatus (e.g., a processing device) 11 which is a part of the system 10 may select one or more noise signals 38 from one or more microphones of a plurality of the noise microphones 14-1, 14-2, . . . , 14-M for the real-time or near real-time broadcasting, such that these one or more noise signals 38 may be combined (e.g., after further processing as disclosed herein) with one or more voice signals 30 provided by the one or more voice microphones 12-1, 12-2, . . . , 12-N. Also, substitution or a partial substitution of the background noise by the pre-recorded noises may be used, as described herein. The event may be a sport event at a stadium, a soccer match, a sporting event in general, a concert, a performance in front of an audience, etc. Moreover, microphones 14-1, 14-2, . . . , 14-M and/or 12-1, 12-2, . . . , 12-N may provide the acoustic signals to the processing device 11 using a wireless connection or a wired connection.

The apparatus 11 may comprise a detector-analyzer 16 which may receive noise signals 32 from the plurality of the noise microphones 14-1, 14-2, . . . , 14-M and may provide indicator signals 34 for the corresponding noise signals, wherein each indicator signal may provide one or more measured parameters of the noise signals 32 measured by a detector-analyzer 16, e.g., an average power, a root-mean-square power, a peak power, one or more characteristics/parameters of the acoustic spectrum such as a number, an amplitude and/or a spectral width of peaks, etc. for corresponding each of the noise signals, as described herein in detail in the discussion of the embodiment A. The detector-analyzer 16 may be a dedicated analog or digital module, a device or a part of a general-purpose computer equipped with appropriate means and suitable application software. Moreover, the detector-analyzer module 16 may be a multi-channel detector-analyzer or it may comprise M identical "sub-modules", each dedicated to evaluation of the noise signal provided by the corresponding one noise microphone of the microphones 14-1, 14-2, . . . , 14-M. It is further noted that an additional analog-to-digital converter (ADC) may be used in front of the detector-analyzer 16 if the detector/analyzer is operated in a digital domain.

The apparatus 11 may further comprise a controller (e.g., a processor) 18 which may compare information comprised in each indicator signal with one or more preset threshold values (e.g., for a measured average power, an RMS power, a peak amplitude, an amplitude and a bandwidth of a spectral peak in the acoustic spectrum, etc.) and then to identify, if available, one or more indicator signals (out of the indicator signals 34 for the corresponding noise signals 32) meeting one or more predetermined criteria, as disclosed in the embodiment A. The controller 37 may coordinate further processing, first, by providing a first control signal 36 to select one or more noise signals (out of all noise signals 32 from the plurality of the dedicated noise microphones 14-1, 14-2, . . . , 14-M) corresponding to the identified indicator signals 34, which may be implemented by a signal selector 20 which may provide one or more selected noise signals 38. Then the controller 18 may provide a third control signal 39 for a modification of the selected one or more noise signals 38 before combining them with the one or more voice signals 30. The modification of the one or more selected noise signals may include, but may not be limited to, possible options: a) statistical averaging, b) adjusting an average power, a peak power, and/or spectral peak(s) in the acoustic spectrum, c) removing one or more undesired frequency components in one or more frequency bands in one or selected noise signals of the selected noise signals 38, and/or d) filling the one or more frequency bands comprising removed frequency components as disclosed in c) with matching one or more pre-recorded noise signals 42, as described herein in detail in the discussion of the embodiment A, using a noise modification module 22 and a database of pre-recorded noises 24. Moreover, this modification may be performed by default such as calculating a statistical averaging as described in option a) of the embodiment A.

Furthermore, if the controller 18 may find that none of the indicator signals 34 for the noise signals 32 meets one or more predetermined criteria (e.g., all indicators exceeding the threshold value THR-2), then the controller 18 may provide a still further second control signal 37 to the database 24 storing a library of the pre-recorded noises in order to provide a matching pre-recorded noise signal 42 or combining this matching pre-recorded noise signal 42 with the one or more voice signals 30 provided by the one or more voice microphones 12-1, 12-2, . . . , 12-N. Also, this matching pre-recorded noise signal 42 may be further modified, e.g., by the noise modification module 22, e.g., per instructions from the controller using the third control signal 39. This further modification may include similar adjustments as for the noise signals as disclosed in detail in options b) through d) of the embodiment A.

Finally, a combiner 26 may combine a noise signal 40, which may be an unmodified one selected noise signal 38-1 as shown in FIG. 2 (e.g., in case when one or more noise signals comprise only one selected noise signal and its one or more measured parameters are all below the corresponding threshold values THR-1), the one or more noise signals after being further modified (e.g., processed per one or more of the options a)-d) disclosed in detail in the embodiment A), or a matching pre-recorded noise signal (original or after being further modified) 42 with the one or more voice signals 30 provided by the one or more voice microphones 12-1, 12-2, . . . , 12-N possibly in the real-time or near real-time.

Implementation of different modules of the apparatus 11 in FIG. 2 may be performed in analog and/or digital domains (analog-to-digital A/D converters may be used if necessary which is not shown in FIG. 2), as well as using hardware and/or software solutions. Also an integrated circuit may comprise all or selected modules of the apparatus 11. Furthermore, the module 16, 18, 20, 22 or 26, of the apparatus (processing device) 11 may be implemented as software, hardware or a combination thereof. Furthermore, the module 16, 18, 20, 22 or 26 may be implemented as a separate block or may be combined with any other modules/blocks of the apparatus (a processing device) 11 or it may be split into several blocks according to their functionality. Moreover, some modules which may be comprised in the apparatus 11 and known to a person skilled in the are not shown in FIG. 2. For example, the processor 18 may use a small processing memory as a part of its operation.

Many variation of the apparatus 11 in FIG. 2 and signal processing may be possible. For example, the processing in FIG. 2 is shown for one audio channel, but more than one channel processing (e.g., using two channels, R and L, for stereo broadcasting) may be used as known to a person skilled in the art. Furthermore, if one noise signal of the selected one or more noise signals 38 in FIG. 2 does not require further processing (i.e. the corresponding parameter(s) for that noise signal being below THR-1) before combining with the one or more noise signals 30, then the controller 18 may not select (or de-select) other noise signals with parameter(s) between THR-1 and THR-2 as explained herein, such that the one selected noise signal 38-1 may be combined with the one or more noise signals 30 without any modification, which would significantly simplify the algorithm.

Figure 3:
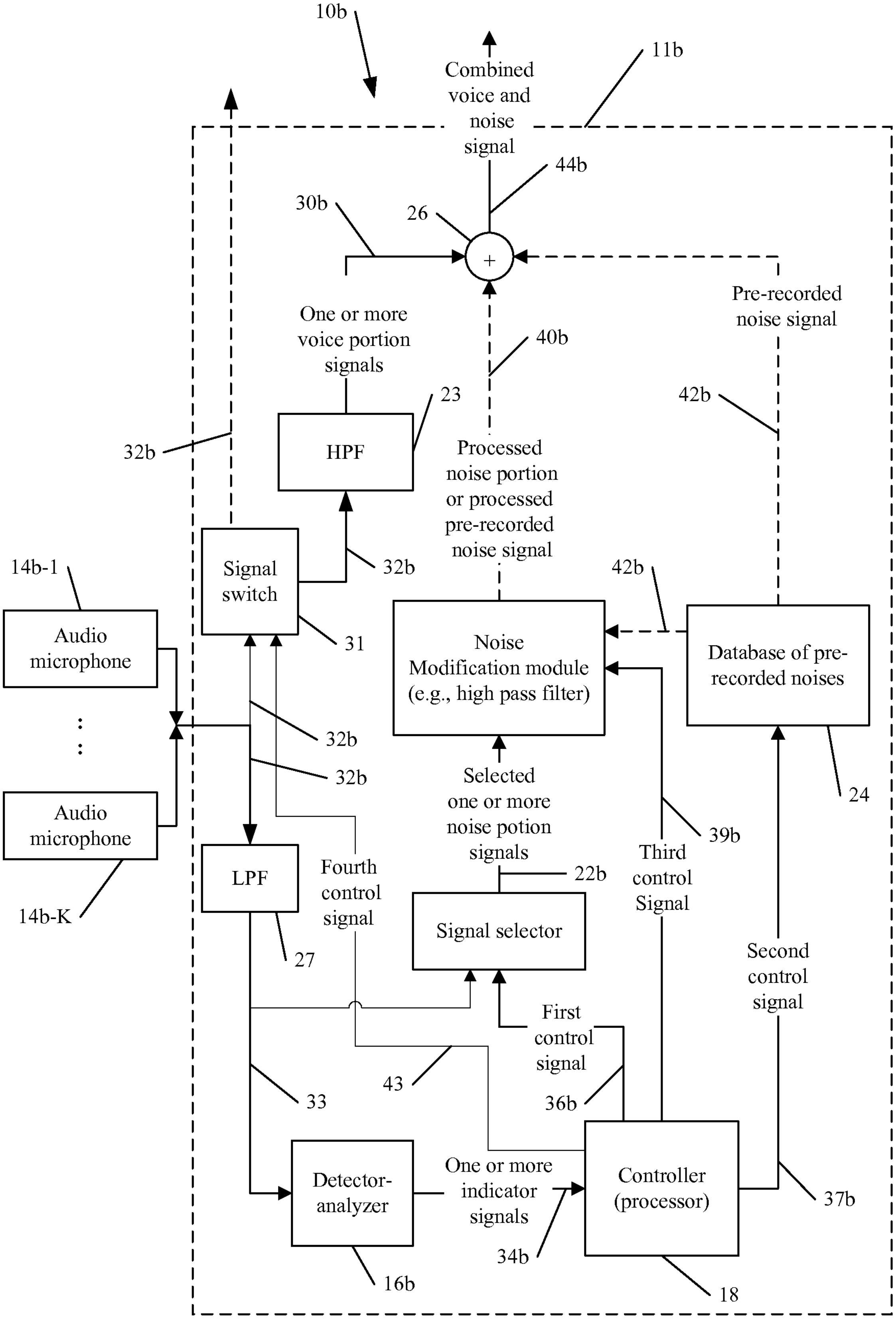
FIG. 3 is a block diagram of a microphone system for noise modification, the system comprising one or more voice microphones and a separate microphone for detecting a background noise during an event, according to an embodiment of the present invention.

FIG. 3 shows an example among others of a block diagram of a microphone system 10*a* for audio modification of a background noise illustrating the embodiment B as disclosed herein. The system 10*a* may comprise one or more voice microphones 12-1, 12-2, . . . , 12-N, N being an integer of a value of one or more, and a separate microphone 14*a* (which may be called a noise microphones) for detecting a background noise during the event. An apparatus (e.g., a processing device) 11*a* which is a part of the system 10*a* may be configured to substitute the noise signal 32*a* from the one microphone 14*a* by a pre-recorded noise signal 42*a* (or by the signal 42*a* after being further modified) for the real-time or near real-time broadcasting, such that the noise signal 38*a*, the modified noise signal 40*a* (e.g., a selected noise signal 38*a* after being further modified as disclosed herein) or the matching pre-recorded noise signal 42*a* (or the signal 42*a* after being further modified) may be combined with one or more voice signals 30 provided by the one or more voice microphones 12-1, 12-2, . . . , 12-N. Also a partial substitution of the background noise by pre-recorded noises may be used as disclosed herein. The event may be a sport event at a stadium, a soccer match, a sporting event in general, a concert, a performance in front of an audience, etc. Also microphones 14*a* and/or 12-1, 12-2, . . . , 12-N may provide the acoustic signals to the processing device 11 using a wireless connection or a wired connection.

The apparatus 11*a* may comprise a detector-analyzer 16*a* which may receive noise signals 32*a* from the noise microphone 14*a* and may provide an indicator signal 34*a* for the noise signal 32*a*, wherein this indicator signal may provide one or more measured parameters of the noise signals 32*a* measured by a detector-analyzer 16*a*, e.g., an average power, a root-mean-square power, a peak power, one or more characteristics/parameters of an acoustic spectrum such as a number, an amplitude and/or a spectral width of peaks, etc., as described herein in detail in the discussion of the embodiment B. The detector-analyzer 16*a* may be a dedicated analog or digital module, a device or a part of a general-purpose computer equipped with appropriate means and suitable application software. It is noted that an additional analog-to-digital converter (ADC) may be used in front of the detector-analyzer 16*a* if the detector/analyzer operated in a digital domain.

Moreover, the apparatus 11*a* may further comprise a controller (e.g., a processor) 18 which may compare information comprised in the indicator signal 34*a* with one or more preset threshold values (e.g., for a measured average power, an RMS power, a peak amplitude, an amplitude and a bandwidth of a spectral peak in the acoustic spectrum, etc.) and then may determine if a substitution of the noise signal 32*a* by a matching pre-recorded noise signal 42*a* is necessary based on a predetermined criterion using this comparing, and to provide a first control signal 36*a* for de-selecting or selecting the noise signal 32*a*; then, if the noise signal 32*a* is de-selected, the controller 18 may provide a second control signal for substituting the noise signal 32*a* by the matching pre-recorded noise signal 42*a*. Moreover, if the noise signal 32*a* is selected, the controller 18 may provide a third control signal 39*a* for modification of the selected noise signal 38*a*, if necessary, before combining with the one or more voice signals 30. The modification of the noise signal may include, but may not be limited to, possible options such as a) adjusting an average power, a peak power, and/or spectral peak(s) in the acoustic spectrum, b) removing one or more undesired frequency components in one or more frequency bands of the noise signal 38*a*, and/or c) filling the one or more frequency bands comprising removed frequency components as disclosed in b) with matching one or more pre-recorded noise signals 42*a*, as described herein in detail in the discussion of the embodiment B, using a noise modification module 22*a* and a database of pre-recorded noises 24.

Furthermore, if the controller 18 may ascertain that the indicator signal 34*a* for the noise signal 32*a* does not meet one or more predetermined criteria (e.g., at least one measured parameter comprised in the indication signal exceeding the second threshold THR-2), then the controller 18 may provide still further a second control signal 37*a* to the database 24 which stores the library of the pre-recorded noises in order to provide a matching pre-recorded noise signal 42*a* for combining said matching pre-recorded noise signal 42*a* (or its modified version as explained herein) with the one or more voice signals 30 provided by the one or more voice microphones 12-1, 12-2, . . . , 12-N. The pre-recorded noise signal 42*a* may be further modified, e.g., by the noise modification module 22*a*, e.g., per instructions from the controller 18 using the third control signal 39*a*. This further modification may include similar adjustments as for the noise signals as disclosed in detail in options b) through d) of the embodiment B.

Finally, a combiner 26 may combine a noise signal 40*a*, which may be an unmodified selected noise signal 32*a* (as shown in FIG. 3), a selected noise signal 38*a* after being further modified (e.g., processed per one or more of the options a)-c) disclosed in detail in the embodiment B, or a matching pre-recorded noise signal (original or after further modified) 42*a* with the one or more voice signals 30 provided by the one or more voice microphones 12-1, 12-2, . . . , 12-N possibly in the real-time or near real-time.

Implementation of different modules of the apparatus 11*a* in FIG. 3 may be performed in analog and/or digital domains (analog-to-digital A/D converters may be used if necessary which is not shown in FIG. 3), as well as using hardware and/or software solutions. Also an integrated circuit may comprise all or selected modules of the apparatus 11*a*. Furthermore, the module 16*a*, 18, 20*a*, 22*a* or 26, of the apparatus (processing device) 11*a* may be implemented as software, hardware or a combination thereof. Furthermore, the module 16*a*, 18, 20*a*, 22*a* or 26 may be implemented as a separate block or may be combined with any other modules/blocks of the apparatus (processing device) 11*a* or it may be split into several blocks according to their functionality. Moreover, some modules which may be comprised in the apparatus 11*a* and known to a person skilled in the art are not shown in FIG. 3. For example, the processor 18 may use a small processing memory as a part of its operation. Furthermore, the processing in FIG. 3 is shown for one audio channel, but more than one channel processing (e.g., using two-channel, R and L, for stereo broadcasting) may be used, as known to a person skilled in the art.

Figure 4:
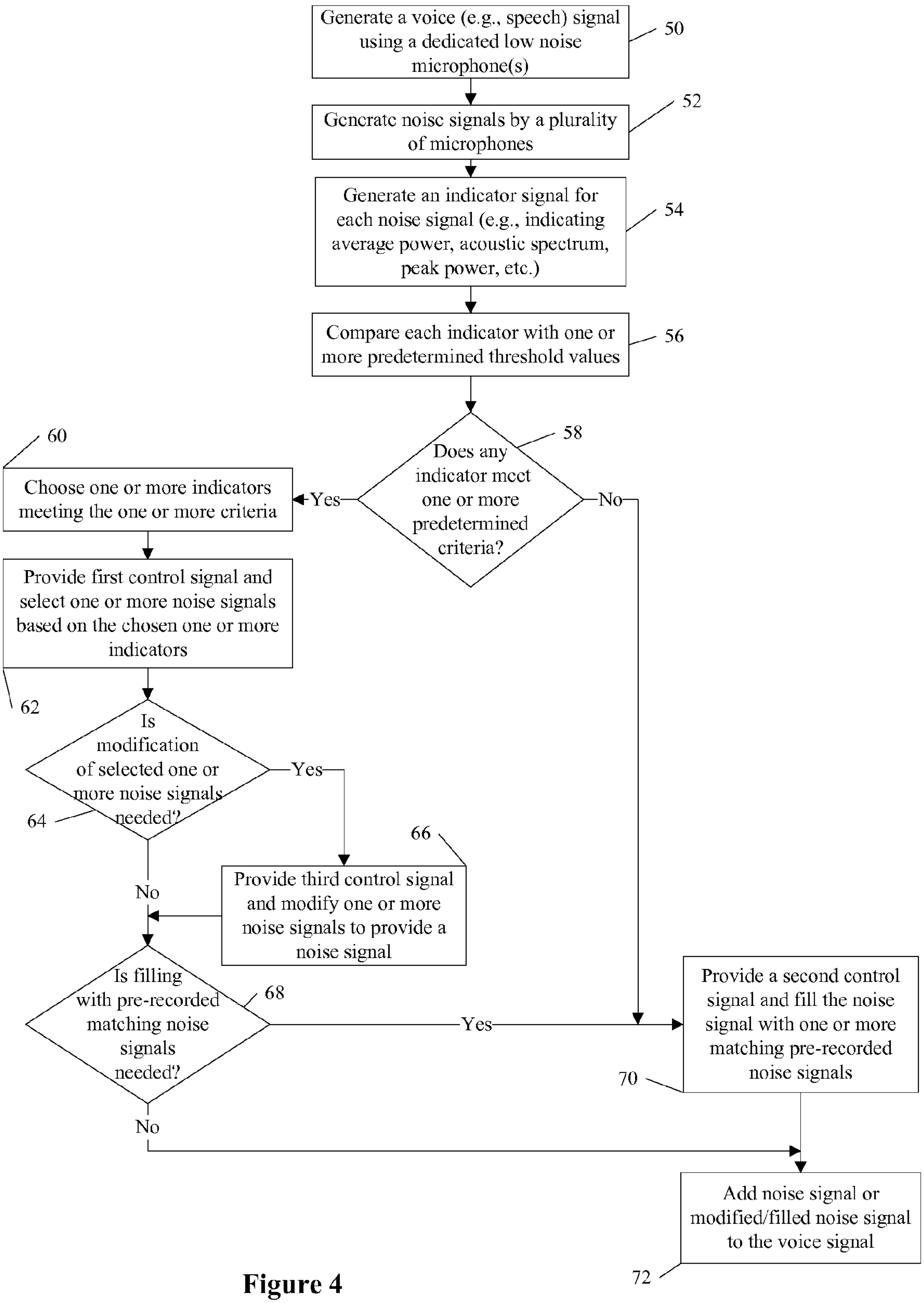
FIG. 4 is a flow chart demonstrating operation of a multiple-microphone system shown for noise modification in FIG. 2, according to an embodiment of the present invention.

FIG. 4 shows a flow chart a flow chart demonstrating operation of a multiple-microphone system for noise modification as shown in FIG. 2, according to an embodiment of the present invention. The flow charts of FIG. 4 only represents one possible scenario among others. It is noted that the order of steps shown in FIG. 4 is not absolutely required, so in principle, the various steps may be performed out of order.

In a method according to the embodiment of the present invention, in a first step 50 (see FIG. 2), one or more dedicated voice microphones 12-1, 12-2, . . . , 12-N (N being an integer of one or more), configured to reject background noise and placed, e.g., in a stadium, may generate and provide one or more voice (e.g., speech) signals. In a next step 52, a plurality of microphones (e.g., dedicated noise microphones) 14-1, 14-2, . . . , 14-M (M being an integer of two or more) may generate and provide one or more noise signals to a detector-analyzer 16.

In a next step 54, the detector-analyzer 16 may generate and provide an indicator signal for each noise signal, e.g., indicating one or more of: an average or RMS power, a peak power, one or more characteristics/parameters of an acoustic spectrum such as a number, an amplitude and/or a spectral width of peaks, etc. In a next step 56, a controller 18 may compare parameter(s) comprised in each indicator signal with one or more predetermined threshold values, as disclosed herein in reference to the embodiment A and FIG. 2.

In a next step 58, it may be determined by the controller 18, whether any indicator may meet one or more predetermined criteria (e.g., if any parameter of the indicator signal is more than THR-1) for measured parameters of any of the noise signals. If this is not the case, the process may move to step 70. However, if it is determined in step 58 that one or more indicators meets one or more predetermined criteria, in a next step 60, these one or more indicators may be identified. Then in a next step 62, the controller 18 may provide a first control signal and one or more noise signals corresponding to the identified one or more indicators are selected.

In a next step 64, it may be further determined by the controller 18, whether any modification of selected one or more noise signals needed (e.g., if any parameter of a particular indicator is between THR-1 and THR-2). If that is not the case, the process may go to step 70. However, if it is determined in step 64 that the modification of any of the selected one or more noise signals is needed, in a next step 66 the controller 18 may provide a third control signal for modifying the one or selected noise signals (which needed modification) and provide a resultant noise signal, e.g., by statistical averaging of the selected/modified noise signals, as disclosed herein in reference to the embodiment A (see options a) and b)).

In a next step 68, it may be further determined by the controller 18, whether filling any of the one or selected noise signals of the one or more noise signals with matching pre-recorded noise signals is needed, e.g., to fill narrow bands filtered in any of the selected noise signals during the modification. If that is not the case, the process may go to step 72. However, if it is determined that filling of any of the one or selected noise signals of the one or more noise signals with matching pre-recorded noise signals is needed, in a next step 70, the controller 18 may generate and provide a second control signal to fill (in response to the input from step 68) or substitute (in response to the input from step 58) the selected noise signal(s) with one or more matching pre-recorded noise signals as disclosed herein in reference to the embodiment A. Finally, in step 72 a combiner 26 may add the one or more noise signals (e.g., one selected and unmodified noise signal), the modified one or more noise signals, the substituted noise signal(s) or the filtered and filled noise signal(s) to the one or more voice signals.

Figure 5:
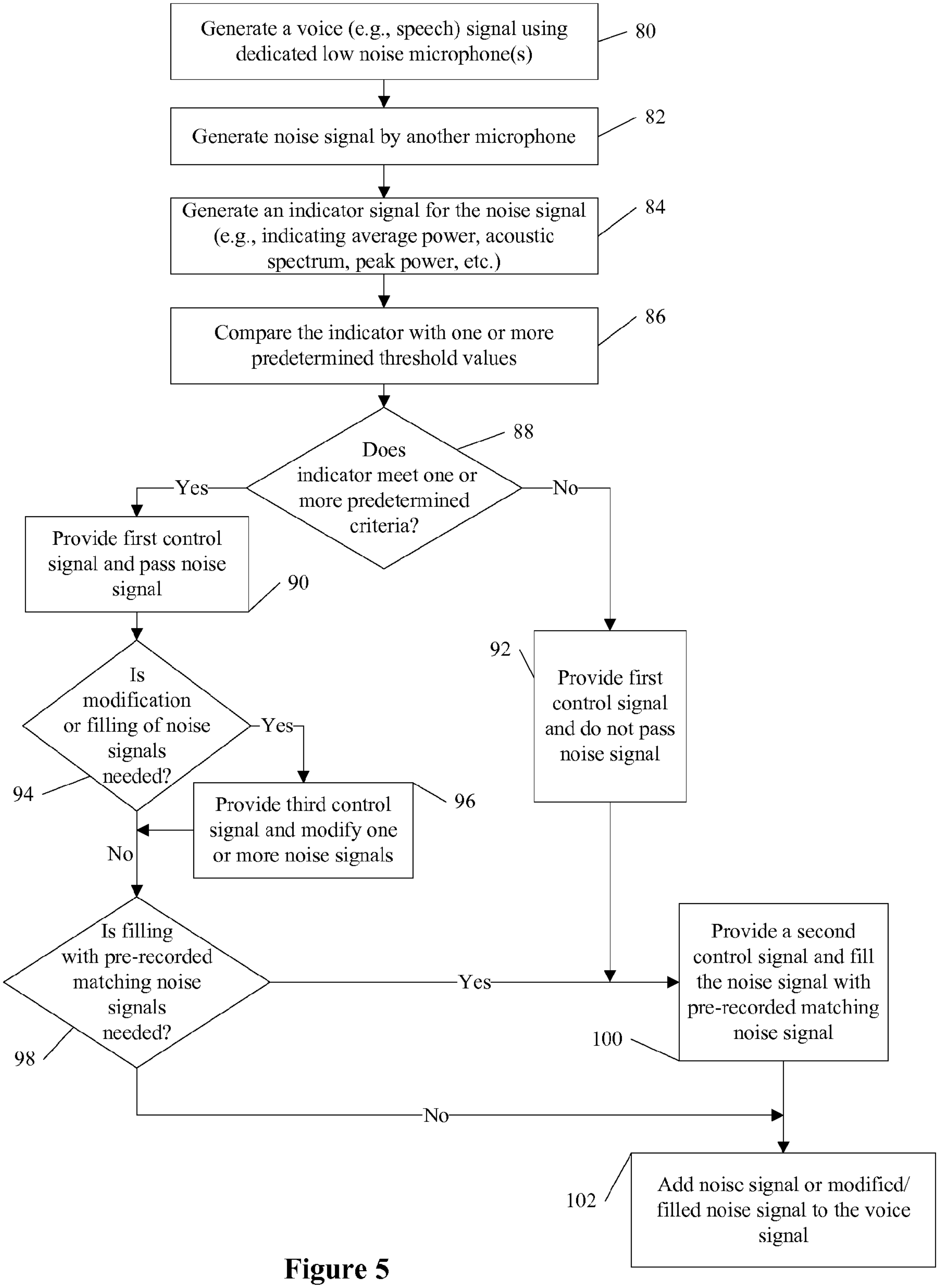
FIG. 5 is a flow chart demonstrating operation of a microphone system for noise modification shown in FIG. 3, according to an embodiment of the present invention.
Figure 6:
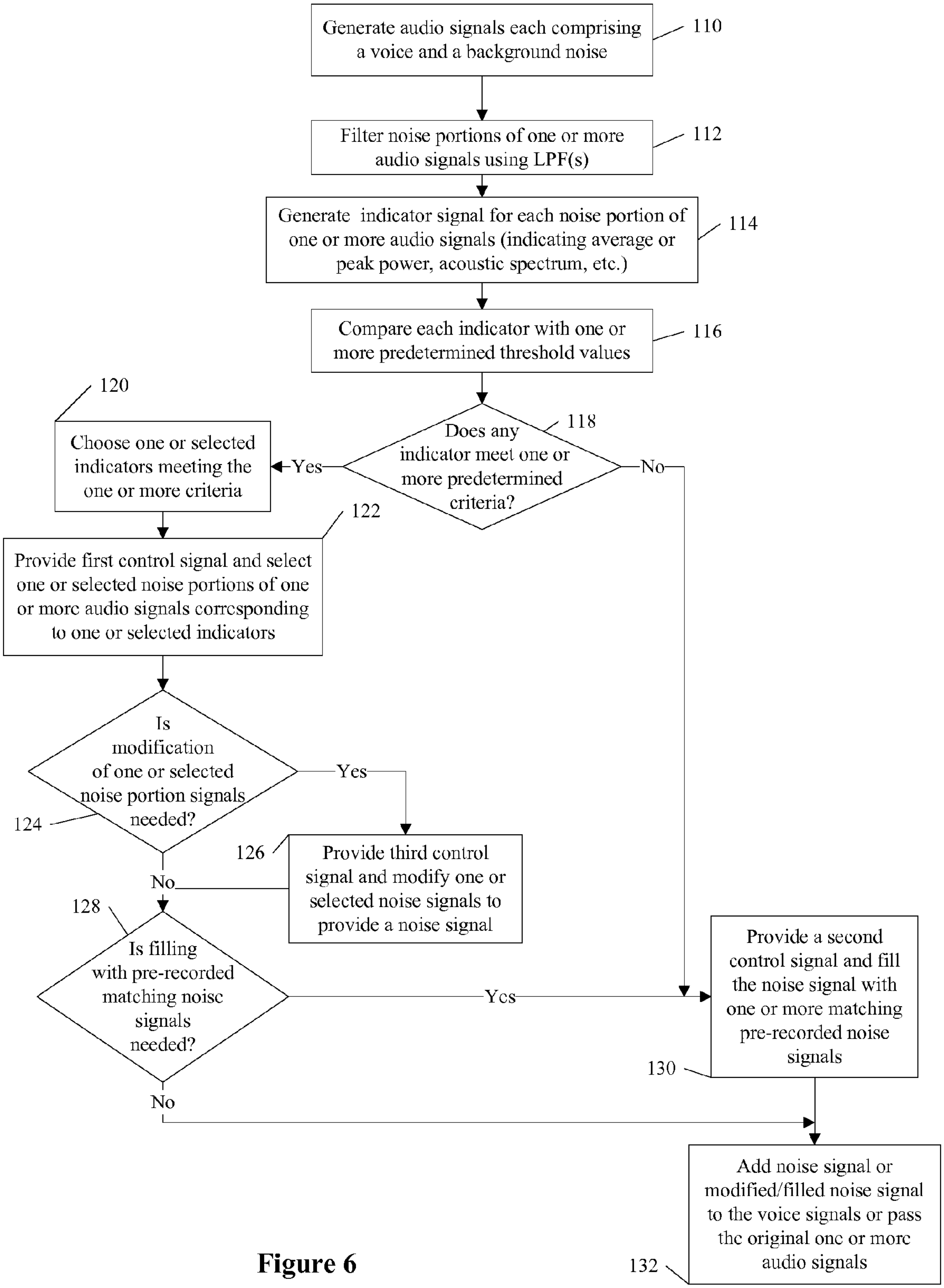

FIG. 5 is a flow chart demonstrating operation of a microphone system for noise modification as shown in FIG. 3, according to an embodiment of the present invention. The flow charts of FIG. 5 only represents one possible scenario among others. It is noted that the order of steps shown in FIG. 5 is not absolutely required, so in principle, the various steps may be performed out of order.

In a method according to the embodiment of the present invention, in a first step 80 (see FIG. 5), one or more dedicated voice microphones 12-1, 12-2, . . . , 12-N (N being an integer of one or more), configured to reject background noise and placed, e.g., in a stadium, may generate and provide one or more voice (e.g., speech) signals. In a next step 82, a microphone (or a dedicated noise microphone) 14*a* may generate and provide a noise signal to a detector-analyzer 16. In a next step 84, the detector-analyzer 16 may generate and provide an indicator signal for the noise signal, e.g., indicating one or more of: its average or RMS power, its speak power, one or more characteristics/parameters of the acoustic spectrum such as a number, an amplitude and/or a spectral width of peaks, etc.

In a next step 86, a controller 18 may compare parameter(s) comprised in this indicator with one or more predetermined threshold values, as disclosed herein in reference to the embodiment A and FIG. 3. In a next step 88, it may be determined by the controller 18, whether this indicator meets one or more predetermined criteria (e.g., if any parameter of the indicator signal is more than THR-1). If this is not the case, a signal selector 20 does not select (or deselect) the noise signal in response to the first control signal from the selector 18 and the process may go to step 100. However, if it is determined in step 88 that the indicator meets one or more predetermined criteria, the controller 18 may provide a first control signal to the selector for selecting this noise signal.

In a next step 94, it may be further determined by the controller 18, whether any modification of the noise signal is needed (e.g., if any parameter of the indicator for the noise signal is between THR-1 and THR-2). If that is not the case, the process may go to step 100. However, if it is determined in step 94 that modification of the selected noise signal is needed, in a next step 96, the controller 18 may provide a third control signal to the noise modification module 22 for modifying this noise signal 38*a* by the noise modification module 22*a* which then may provide a resultant noise signal 40*a*, as disclosed herein in reference to the embodiment B (e.g., see option b)) and FIG. 3.

In a next step 98, it may be further determined by the controller 18, whether filling of the noise signal with matching pre-recorded noise signals is needed, e.g., to fill narrow band(s) filtered in the selected noise signals during the modification. If that is not the case, the process may go to step 102. However, if it is determined that filling of the noise signal of the noise signal with the matching pre-recorded noise signal(s) is needed, in a next step 100, the controller 18 may generate and provide a second control signal to fill (in response to the input from step 98) or substitute (in response to the input from step 92) the noise signal with one or more matching pre-recorded noise signals as disclosed herein in reference to the embodiment B (filling or substitution may be performed, e.g., by the noise modification module 22*a* as shown in FIG. 3). Finally, in step 102 a combiner 26 may add the noise signal, the modified noise signal, the substituted noise signal or the filled noise signal to the one or more voice signals.

As explained above, the invention may provide a method and a corresponding equipment comprising various modules providing the functionality for performing the method. Each disclosed module may be implemented as one or more of: software, firmware or hardware. In particular, in the case of firmware or software, one embodiment may be provided for a computer readable medium or a computer readable storage structure comprising computer readable instructions using a computer program code (i.e., the software or firmware) thereon for execution by a computer processor.

It is noted that various embodiments of the present invention recited herein may be used separately, combined or selectively combined for specific applications. It is further noted that the above-described arrangements are only illustrative of the application of the principles of the present invention. Numerous modifications and alternative arrangements may be devised by those skilled in the art without departing from the scope of the present invention, and the appended claims are intended to cover such modifications and arrangements.

The invention claimed is:

1. A system comprising:

a first grouping of one or more microphones operatively configured to transform acoustical background noise into electrical noise signals appearing at an output of each of said first grouping of microphones;

a second grouping of one or more microphones operatively configured to transform acoustical voice signals into electrical voice signals appearing at an output of each of said second grouping of microphones;

a detector-analyzer, electrically coupled to each of said outputs of said first grouping of microphones, that measures said electrical noise signals and provides an indicator signal describing at least one parameter of said electrical noise signals;

a controller, electrically coupled to said detector-analyzer, said controller comprising a comparator that compares said indicator signal with a plurality of predetermined threshold levels that define N adjacent, non-overlapping ranges, said comparator generates control signals indicative of a relationship between said indicator signal and said plurality of predetermined threshold levels and processes said electrical noise signal as determined by said control signals;

a database storing a plurality of prerecorded noise signals, operatively connected to said controller, and operatively configured to select and playback one of said plurality of prerecorded noise signals in response to said control signal; and a combiner connected to said second grouping of one or more microphones and said controller, said combiner sums said processed electrical noise signal, and said electrical voice signals, and outputs a sum.

2. A system in accordance with claim 1 wherein said parameter of said electrical noise signal comprises one or more of 1) average power, 2) root-mean-square power, 3) peak power and 4) spectral/temporal characteristics of said noise signal.

3. A system in accordance with claim 1 wherein two of said plurality of predetermined threshold levels define three said adjacent non-overlapping, ranges comprising a lower range, a middle range, and an upper range.

4. A system in accordance with claim 3 wherein, when said indicator signal is within said lower range, method of said processing comprises frequency-independent positive or negative amplification.

5. A system in accordance with claim 3 wherein, when said indicator signal is within said middle range, method of said processing comprises modification of said electrical noise signal.

6. A system in accordance with claim 3 wherein, when said indicator signal is within said upper range, method of said processing comprises substitution of a replacement signal for said electrical noise signal.

7. A system in accordance with claim 5 wherein, said modification of said electrical noise signal comprises application of one or more of frequency independent gain/attenuation, frequency selective gain/attenuation, and substitution of said prerecorded noise signals for frequency selected portions of said electrical noise signal.

8. A system in accordance with claim 6 wherein, said replacement signal is one of said plurality of prerecorded noise signals.

9. A method comprising:

obtaining an electrical noise signal from a first grouping of microphones;

obtaining an electrical voice signal from a second grouping of microphones;

detecting and analyzing said electrical noise signal and generating one or more indicator signals in response to said detecting and analyzing, said one or more indicator signals describing at least one parameter of said electrical noise signal;

comparing a level of said one or more indicator signals with a plurality of predetermined threshold levels that define N adjacent, non-overlapping ranges and thereby determining which of a plurality of the non-overlapping ranges said one or more indicator signal falls within;

generating one or more control signals reflecting the range in which said one or more indicator signals falls;

substituting said electrical noise signal by selecting a prerecorded noise signal from a plurality of prerecorded noise signals based on the range reflected by the control signal; and combining and outputting said selected prerecorded noise signal and said electrical voice signal.

10. A method in accordance with claim 9 wherein said parameter of electrical noise signal comprises one or more of 1) average power, 2) root-mean-square power, 3) peak power and 4) spectral/temporal characteristics of said noise signal.

11. A method in accordance with claim 9 wherein two of said predetermined threshold levels define three said adjacent non-overlapping, ranges comprising a lower range, a middle range, and an upper range.

12. A method in accordance with claim 11 wherein, when said indicator signal is within said lower range, said processing comprises frequency-independent positive or negative amplification.

13. A method in accordance with claim 11 wherein, when said indicator signal is within said middle range, said processing comprises modification of said electrical noise signal.

14. A method in accordance with claim 11 wherein, when said indicator signal is within said upper range, said processing comprises substitution of a replacement electrical signal for said electrical noise signal.

15. A method in accordance with claim 13 wherein, said modification of said electrical noise signal comprises application of one or more of frequency independent gain/attenuation, frequency selective gain/attenuation, and substitution of said prerecorded noise signals for frequency selected portions of said electrical noise signal.

16. A non-transitory computer readable storage-medium encoded with a computer program comprising computer readable instructions recorded thereon executing, by a computer a method comprising:

obtaining an electrical noise signal from a first grouping of microphones;

obtaining an electrical voice signal from a second grouping of microphones;

detecting and analyzing said electrical noise signal and generating one or more indicator signals in response to said detecting and analyzing, said one or more indicator signals describing at least one parameter of said electrical noise signal;

comparing a level of said one or more indicator signals with a plurality of predetermined threshold levels that define N adjacent, non-overlapping ranges and thereby determining which of a plurality of the non-overlapping ranges said one or more indicator signal falls within;

generating one or more control signals reflecting the range in which said one or more indicator signals falls;

substituting said electrical noise signal by selecting a prerecorded noise signal from a plurality of prerecorded noise signals based on the range reflected by the control signal; and combining and outputting said selected prerecorded noise signal and said electrical voice signal.

* * * * *